United States Patent
Moszner et al.

(10) Patent No.: US 11,141,354 B2
(45) Date of Patent: *Oct. 12, 2021

(54) DENTAL MATERIALS WITH IMPROVED MECHANICAL PROPERTIES

(71) Applicant: Ivoclar Vivadent AG, Schaan (LI)

(72) Inventors: Norbert Moszner, Triesen (LI); Alexandros Gianasmidis, Balgach (CH); Michael Westphal, Feldkirch (AT); Deborah Kalberer, Wangs (CH)

(73) Assignee: Ivoclar Vivadent AG, Schaan (LI)

( * ) Notice: Subject to any disclaimer, the term of this patent is extended or adjusted under 35 U.S.C. 154(b) by 0 days.

This patent is subject to a terminal disclaimer.

(21) Appl. No.: 16/781,112

(22) Filed: Feb. 4, 2020

(65) Prior Publication Data

US 2020/0253834 A1 Aug. 13, 2020

(30) Foreign Application Priority Data

Feb. 7, 2019 (EP) ..................................... 19156082

(51) Int. Cl.
*A61K 6/61* (2020.01)
*A61K 6/887* (2020.01)

(52) U.S. Cl.
CPC ................ *A61K 6/61* (2020.01); *A61K 6/887* (2020.01)

(58) Field of Classification Search
CPC ....................................................... A61K 6/61
See application file for complete search history.

(56) References Cited

U.S. PATENT DOCUMENTS

| | | | | |
|---|---|---|---|---|
| 3,991,008 A | * | 11/1976 | Temin | C08K 13/02 523/115 |
| 5,705,581 A | * | 1/1998 | Fife | C07C 233/38 526/248 |
| 6,815,470 B2 | * | 11/2004 | Ibaragi | A61K 6/30 523/118 |
| 7,275,932 B2 | * | 10/2007 | Jin | A61K 6/54 433/228.1 |
| 7,498,367 B2 | | 3/2009 | Qian | |
| 8,247,470 B2 | | 8/2012 | Yarimizu | |
| 2003/0134933 A1 | | 7/2003 | Jin et al. | |
| 2007/0040151 A1 | | 2/2007 | Utterodt et al. | |
| 2007/0100019 A1 | | 5/2007 | Sun | |
| 2008/0003542 A1 | | 1/2008 | Jin et al. | |
| 2010/0311864 A1 | | 12/2010 | Arita et al. | |

FOREIGN PATENT DOCUMENTS

| | | |
|---|---|---|
| CN | 103834308 A | 6/2014 |
| JP | 2014152106 A * | 8/2014 |
| JP | 2014152106 A | 8/2014 |

OTHER PUBLICATIONS

English machine translation of Okishio (JP 2014-152106) (Year: 2014).*

* cited by examiner

*Primary Examiner* — Michael F Pepitone
(74) *Attorney, Agent, or Firm* — Ann M. Knab; Thad McMurray

(57) ABSTRACT

Radically polymerizable dental material, which contains a combination of a thiourea derivative, a hydroperoxide and at least one peroxide as well as a transition metal compound as initiator system for the radical polymerization.

21 Claims, No Drawings

DENTAL MATERIALS WITH IMPROVED MECHANICAL PROPERTIES

CROSS-REFERENCE TO RELATED APPLICATIONS

This application claims priority to European patent application No. 19156082.0 filed on Feb. 7, 2019, the disclosure of which is incorporated herein by reference in its entirety.

FIELD OF INVENTION

The present invention relates to radically polymerizable compositions with improved setting behaviour and improved mechanical properties which are suitable in particular as dental materials, for example as prosthesis materials, cements, adhesives and composites for direct fillings. The compositions contain a redox system as initiator for the radical polymerization, which comprises a hydroperoxide, a thiourea derivative and a peroxide.

BACKGROUND

The main areas of use of polymers in the dental field are removable prosthetics (e.g. teeth and prosthesis base materials) and fixed prosthetics (e.g. veneering materials, crowns or cements), filling materials (e.g. direct or indirect filling composites, fixing cements or adhesives) or auxiliary materials (e.g. impression materials). The polymers are usually obtained by radical polymerization of suitable compositions which contain a polymerizable organic matrix, usually a mixture of monomers, initiator components and stabilizers.

Methyl methacrylate (MMA) (prosthesis materials), mixtures of functionalized monomers, such as e.g. 2-hydroxyethyl methacrylate (HEMA), or acid-group-containing adhesive monomers, such as e.g. 10-methacryloyloxydecyl dihydrogen phosphate (MDP), with dimethacrylates (adhesives) or mixtures which contain exclusively dimethacrylates (composite cements and filling composites) are usually used as monomers. Dimethacrylates often used are 2,2-bis[4-(2-hydroxy-3-methacryloyloxypropyl)phenyl]propane (bis-GMA) and 1,6-bis-[2-methacryloyloxyethoxycarbonylamino]-2,2,4-trimethylhexane (UDMA), which have a high viscosity and result in polymerizates with very good mechanical properties. Above all, triethylene glycol dimethacrylate (TEGDMA), 1,10-decanediol dimethacrylate (D3MA) or bis-(3-methacryloyloxymethyl)tricyclo-[5.2.1.02,6]decane (DCP) are used as reactive diluents.

Methacrylate-based dental materials are cured by radical polymerization, wherein radical photoinitiators (light curing, direct filling composites and adhesives), thermal initiators (indirect composites or prosthesis materials) or redox initiator systems (composite cements) are used depending on the field of use. The combination of photoinitiators with redox initiators is also known, e.g. when filling deep cavities.

Redox systems are used above all when there is the risk of incomplete curing, because of a low monomer reactivity e.g. in the case of prosthesis materials or because of insufficient irradiation in the case of fixing cements.

In order to guarantee a sufficient storage stability of the materials, materials based on redox initiators are usually used as so-called two-component systems (2C systems), wherein the oxidant (peroxide or hydroperoxide) and the reducing agent (amines, sulfinic acids, barbiturates, thiourea etc.) are incorporated into two separate components. These components are mixed with each other shortly before use. The two components must be matched such that their homogeneous blending and use is easily possible and that a processing time sufficient for dental purposes is achieved. By the processing time is meant the period of time between the blending of the two components and the start of curing of the mixed material. It should lie in a range of from approximately 90 to 150 s. On the other hand, the curing time, i.e. the period until complete hardening of the materials, must not be too long. A curing time of approx. 3 to 5 min is optimal.

For a long time, redox initiator systems which are based on a mixture of dibenzoyl peroxide (DBPO) with tertiary aromatic amines, such as e.g. N,N-diethanol-p-toluidine (DEPT), N,N-dimethyl-sym.-xylidine (DMSX) or N,N-diethyl-3,5-di-tert.-butylaniline (DABA) have primarily been used for dental composite cements. With DBPO/amine-based redox initiator systems the processing and curing time can be set relatively well in combination with phenolic inhibitors. A disadvantage of such DBPO/amine systems is the discolorations which are caused by a slow oxidation of the amines. Moreover, the radical formation in the case of DBPO/amine-based redox initiator systems is impaired by acids and thus also by acid monomers, which are normally used to prepare enamel-dentine adhesives. The amine component is protonated by an acid-base reaction and thereby deactivated.

The above disadvantages can be partially overcome with hydroperoxide redox initiator systems, because no tertiary amines are needed as reducing agent. Moreover, hydroperoxides are more thermally stable than peroxides. Cumene hydroperoxide has for example a 10-hour half-life temperature $T_{1/2}$ of 158° C.; the 10-hour half-life temperature $T_{1/2}$ of DBPO is only 73° C.

DE 26 35 595 C2 and corresponding U.S. Pat. No. 3,991,008, which is hereby incorporated by reference in its entirety, discloses polymerizable dental filling compounds which contain a substituted thiourea reducing agent in combination with a hydroperoxide oxidant as initiator system. The materials are said to have an improved colour stability, an excellent cure rate and an improved storage stability.

EP 1 693 046 B1 and corresponding U.S. Pat. No. 7,498,367, which is hereby incorporated by reference in its entirety, discloses dental cements and core build-up materials which contain a (2-pyridyl)-2-thiourea derivative in combination with a hydroperoxide, in which the hydroperoxide group is bonded to a tertiary carbon atom.

WO 2007/016508 A1 and corresponding US 2007100019, which is hereby incorporated by reference in its entirety, discloses a polymerizable dental composition which contains a thiourea derivative in combination with a hydroperoxide as initiator system. The composition does not contain monomers with acid groups.

According to EP 1 754 465 B1 and corresponding U.S. Pat. No. 4,582,823, which is hereby incorporated by reference in its entirety, the cumene hydroperoxide/acetyl thiourea system has unusably slow curing kinetics. The addition of soluble copper compounds is proposed to overcome this problem.

U.S. Pat. No. 7,275,932 B2, which is hereby incorporated by reference in its entirety, proposes the use of hydroperoxides and thiourea derivatives in combination with an acid compound as accelerator. Preferred acid compounds are acrylates and methacrylates with acid groups such as e.g. methacrylic acid.

EP 2 233 544 A1 and corresponding U.S. Pat. No. 8,247,470, which is hereby incorporated by reference in its entirety, and EP 2 258 336 A1 and corresponding US 20100311864, which is hereby incorporated by reference in its entirety, disclose dental materials which contain a hydroperoxide and a thiourea derivative in combination with a vanadium compound as accelerator.

To avoid the disadvantages associated with organic peroxides and tertiary amines, U.S. Pat. No. 6,815,470 B2, which is hereby incorporated by reference in its entirety, proposes the use of an aryl borate in combination with an acid compound and a peroxide as initiator system. The aryl borate is said to form an aryl borane by reaction with the acid compound, which releases polymerizable radicals when reacted with oxygen. Polymerizable monomers which have acid groups can be used as acid compound.

Despite the numerous efforts to overcome the disadvantages associated with peroxides and amine accelerators, no initiator system for dental purposes has yet been found which is satisfactory in every respect.

SUMMARY

The object of the invention is to provide dental materials which do not have the disadvantages of the state of the art. The materials are on the one hand to have a high storage stability and to display no discolorations, but at the same time to harden rapidly and still have a processing time that is suitable for dental purposes. In addition, the materials are also in particular to have good mechanical properties.

DETAILED DESCRIPTION

This object is achieved by radically polymerizable dental materials which contain a combination of a thiourea derivative, a hydroperoxide, a peroxide and at least one transition metal compound as initiator system for the radical polymerization. According to the invention it was surprisingly found that the reactivity of an initiator system based on a hydroperoxide and a thiourea derivative can be considerably accelerated by the addition of a small quantity of a peroxide. It has moreover been found that the addition of a transition metal compound yields materials which have substantially improved mechanical properties after hardening.

Hydroperoxides preferred according to the invention are compounds of the formula R—(OOH)$_n$, in which R is an aliphatic or aromatic hydrocarbon radical and n is 1 or 2. Preferred radicals R are alkyl and aryl groups. The alkyl groups can be straight-chain, branched or cyclic. Cyclic alkyl radicals can be substituted by aliphatic alkyl groups. Alkyl groups with 4 to 10 carbon atoms are preferred. Aryl groups can be unsubstituted or substituted by alkyl groups. Preferred aromatic hydrocarbon radicals are benzene radicals which are substituted with 1 or 2 alkyl groups. The aromatic hydrocarbon radicals preferably contain 6 to 12 carbon atoms. Particularly preferred hydroperoxides are t-amyl hydroperoxide, 1,1,3,3-tetramethylbutyl hydroperoxide, t-butyl hydroperoxide, t-hexyl peroxide, 2,5-dimethyl-2,5-di(hydroperoxy)hexane, diisopropylbenzene monohydroperoxide, paramenthane hydroperoxide, p-isopropylcumene hydroperoxide and mixtures thereof. Cumene hydroperoxide (CHP) is quite particularly preferred.

Peroxides preferred according to the invention are compounds of the formula R'—(O—O—R")$_m$, in which R' and R" in each case represent an aliphatic or aromatic hydrocarbon radical or an acyl group and m is 1 or 2. Diacyl peroxides are particularly preferred. Preferred aliphatic hydrocarbon radicals are radicals with 3 to 8 carbon atoms, preferred aromatic hydrocarbon radicals are radicals with 6 to 12 carbon atoms, wherein benzene radicals which are substituted with 1 or 2 alkyl groups are particularly preferred. Preferred acyl groups are groups which contain 2 to 20 carbon atoms.

Preferred peroxides in which R' and R" in each case represent an aliphatic or aromatic hydrocarbon radical are α,α-bis(t-butylperoxy)diisopropylbenzene, dicumene peroxide, 2,5-dimethyl-2,5-bis(t-butylperoxy)hexane, t-butyl cumyl peroxide, di-t-butyl peroxide, 2,5-dimethyl-2,5-bis(t-butylperoxy)hexyne-3.

Preferred diacyl peroxides are isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide and mixtures thereof. A quite particularly preferred peroxide is benzoyl peroxide (DBPO). Hydroperoxides are not peroxides within the meaning of the invention.

Preferred thiourea derivatives are the compounds listed in paragraph [0009] in EP 1 754 465 A1. Particularly preferred thiourea derivatives are acetyl, allyl, pyridyl and phenyl thiourea, hexanoyl thiourea and mixtures thereof. Acetyl thiourea (ATU) is quite particularly preferred.

Thiourea derivatives with the formula

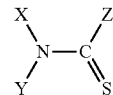

in which
X is H or Y,
Y is an alkyl radical with 1 to 8 carbon atoms, a cycloalkyl radical with 5 or 6 carbon atoms, a chlorine-, hydroxy- or mercapto-substituted alkyl radical with 1 to 8 carbon atoms, an alkenyl radical with 3 to 4 carbon atoms, an aryl radical with 6 to 8 carbon atoms, a chlorine-, hydroxy-, methoxy- or sulfonyl-substituted phenyl radical, an acyl radical with 2 to 8 carbon atoms, a chlorine- or methoxy-substituted acyl radical, an aralkyl radical with 7 to 8 carbon atoms or a chlorine- or methoxy-substituted aralkyl radical, and
Z is NH$_2$, NHX or NX$_2$
are further preferred.

Transition metal compounds preferred according to the invention are compounds which are derived from transition metals which have at least two stable oxidation states. Compounds of the elements copper, iron, cobalt, nickel and manganese are particularly preferred. These metals have the following stable oxidation states: Cu(I)/Cu(II), Fe(II)/Fe(III), Co(II)/Co(III), Ni(II)/Ni(III), Mn(II)/Mn(III). Materials which contain at least one copper compound are particularly preferred.

The transition metals are preferably used in the form of their salts. Preferred salts are the nitrates, acetates, 2-ethylhexanoates and halides, wherein chlorides are particularly preferred.

The transition metals can furthermore advantageously be used in complexed form, wherein complexes with chelate-forming ligands are particularly preferred. Preferred simple ligands for complexing the transition metals are 2-ethylhexanoate and THF. Preferred chelate-forming ligands are 2-(2-aminoethylamino)ethanol, aliphatic amines, particularly preferably 1,1,4,7,10,10-hexamethyltriethylenetetramine (HMTETA), N,N,N',N",N"-pentamethyldiethylenetriamine (PMDETA), tris[2-(dimethylamino)ethyl]amine (Me₆TREN), N,N,N',N'-tetramethylethylenediamine (TMEDA), 1,4,8,11-tetraaza-1,4,8,11-tetramethylcyclotetradecane (Me4CYCLAM), diethylenetriamine (DETA), triethylenetetramine (TETA) and 1,4,8,11-tetraazacyclotetradecane (CYCLAM); pyridine-containing ligands, particularly preferably N,N,N',N'-tetrakis(2-pyridylmethyl) ethylenediamine (TPEN), N,N-bis(2-pyridylmethyl)amine (BPMA), N,N-bis(2-pyridylmethyl)octylamine (BPMOA), 2,2'-bipyridine and 8-hydroxyquinoline. Quite particularly preferred ligands are acetylacetone, dimethylglyoxime and 1,10-phenanthroline.

In the case of electrically neutral ligands, the charge of the transition metal ions must be balanced by suitable counterions. For this, the above-named ions which are used to form salts are preferred, wherein acetates and chlorides are particularly preferred. Chlorides and complexes are characterized by a relatively good solubility in monomers, which are used to prepare dental materials.

Instead of the transition metal complexes, non-complex salts of the transition metals in combination with complex-forming organic compounds can be used to prepare the dental materials, preferably in combination with the above-named chelate-forming compounds. The organic ligands form the catalytically active complexes when mixed with the transition metal salts. The use of such combinations of transition metal salts and organic ligands is preferred.

Transition metal compounds of the metals copper, iron, cobalt and nickel are preferred.

Preferred copper salts are CuCl, CuBr, $CuCl_2$, $CuBr_2$, $CuI_2$, Cu(II) carboxylates (e.g. of acetic acid or 2-ethylhexanoic acid). Preferred copper complexes are complexes with the ligands acetylacetone, phenanthroline (e.g. 1,10-phenanthroline (phen)), the aliphatic amines, such as e.g. 1,1,4,7,10,10-hexamethyltriethylenetetramine (HMTETA), N,N,N',N'',N''-pentamethyldiethylenetriamine (PMDETA), tris[2-(dimethylamino)ethyl]amine (Me₆TREN).

Preferred iron salts are $FeCl_3$, $FeBr_2$ and $FeCl_2$. Preferred iron complexes are complexes with the ligands acetylacetone, triphenylphosphine, 4,4'-di(5-nonyl)-2,2'-bipyridine (dNbpy) or 1,3-diisopropyl-4,5-dimethylimidazol-2-ylidene (PrIlm). The complexes $Fe(acac)_2$ and $FeCl_2(PPh_3)_2$ are quite particularly preferred.

Preferred nickel salts are $NiBr_2$ and $NiCl_2$, preferred nickel complexes are nickel acetylacetonate and $NiBr_2(PPh_3)_2$.

In all cases, those complexes in which the respective transition metal is present in its most stable oxidation state are preferred. Complexes of $Cu^{2+}$, $Fe^{3+}$, $Ni^{2+}$ and $Co^{3+}$ are thus preferred.

According to the invention, copper compounds, copper complexes and in particular mixtures of copper salts and complexing organic ligands are particularly preferred.

The hydroperoxide is preferably used in a quantity of from 0.01 to 5.0 wt.-%, particularly preferably 0.05 to 4.0 wt.-% and quite particularly preferably 0.1 to 3.0 wt.-%. The thiourea derivative is preferably used in a molar quantity of from 25 to 100 mol-%, preferably 50 to 100 mol-%, relative to the molar quantity of hydroperoxide, quite particularly preferably in the same molar concentration as the hydroperoxide. The peroxide is preferably used in a quantity of from 1 to 15 wt.-%, preferably 1 to 10 wt.-% and quite particularly preferably from 2 to 8 wt.-%, relative to the mass of the hydroperoxide.

The transition metal compound is preferably used in a quantity of from 0.0001 to 1 wt.-%, preferably 0.0005 to 0.500 wt.-% and particularly preferably 0.0007 to 0.020 wt.-%, relative to the total mass of the composition.

The initiator system according to the invention is particularly suitable for curing radically polymerizable compositions.

Compositions according to the invention preferably contain at least one radically polymerizable monomer in addition to the initiator system. Compositions which contain at least one mono- or multifunctional (meth)acrylate as radically polymerizable monomer are particularly preferred. By monofunctional (meth)acrylates is meant compounds with one, by multifunctional (meth)acrylates is meant compounds with two or more, preferably 2 to 4, radically polymerizable groups. According to a quite particularly preferred embodiment, the compositions according to the invention contain at least one dimethacrylate or a mixture of mono- and dimethacrylates. Materials which are to be hardened intraorally preferably contain mono- and/or multifunctional methacrylates as radically polymerizable monomer.

Preferred mono- or multifunctional (meth)acrylates are methyl, ethyl, 2-hydroxyethyl, butyl, benzyl, tetrahydrofurfuryl or isobornyl (meth)acrylate, p-cumylphenoxyethylene glycol methacrylate (CMP-1E), 2-(2-biphenyloxy)ethyl methacrylate, bisphenol A dimethacrylate, bis-GMA (an addition product of methacrylic acid and bisphenol A diglycidyl ether), ethoxylated or propoxylated bisphenol A dimethacrylate, such as e.g. 2-[4-(2-methacryloyloxyethoxyethoxy)phenyl]-2-[4-(2-methacryloyloxyethoxy)-phenyl] propane) (SR-348c, from Sartomer; contains 3 ethoxy groups) and 2,2-bis[4-(2-methacryloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), di-, tri- or tetraethylene glycol dimethacrylate, trimethylolpropane trimethacrylate, pentaerythritol tetramethacrylate as well as glycerol di- and trimethacrylate, 1,4-butanediol dimethacrylate, 1,10-decanediol dimethacrylate (D3MA), bis(methacryloyloxymethyl)tricyclo-[5.2.1.0²,⁶]decane (DCP), polyethylene glycol or polypropylene glycol dimethacrylates, such as e.g. polyethylene glycol 200 dimethacrylate or polyethylene glycol 400 dimethacrylate (PEG 200 DMA or PEG 400 DMA) or 1,12-dodecanediol dimethacrylate, or a mixture thereof.

According to an embodiment the compositions according to the invention preferably additionally contain one or more acid-group-containing radically polymerizable monomers (adhesive monomers) in addition to the above-named monomers. These give the materials self-adhesive and/or self-etching properties. Acid-group-containing monomers are therefore particularly suitable for the preparation of self-adhesive dental materials, such as e.g. fixing cements.

Preferred acid-group-containing monomers are polymerizable carboxylic acids, phosphonic acids and phosphoric acid esters as well as their anhydrides. Preferred carboxylic acids and carboxylic acid anhydrides are 4-(meth)acryloyloxyethyl trimellitic acid anhydride, 10-methacryloyloxydecylmalonic acid, N-(2-hydroxy-3-methacryloyloxypropyl)-N-phenylglycine, 4-vinylbenzoic acid. Preferred phosphoric acid esters are 2-methacryloyloxyethylphenyl hydrogen phosphate, 10-methacryloyloxydecyl dihydrogen phosphate (MDP) and dipentaerythritol pentamethacryloyloxyphosphate. Preferred phosphonic acids are 4-vinylbenzylphosphonic acid, 2-[4-(dihydroxyphosphoryl)-2-oxa-butyl]-acrylic acid and their amides, esters, such as e.g. 2-[4-(dihydroxyphosphoryl)-2-oxa-butyl]-acrylic acid-2,4, 6-trimethylphenyl ester.

Particularly preferred acid-group-containing monomers are 4-vinylbenzylphosphonic acid, 2-[4-(dihydroxyphosphoryl)-2-oxa-butyl]-acrylic acid and their amides, esters, such as e.g. 2-[4-(dihydroxyphosphoryl)-2-oxa-butyl]-acrylic acid-2,4,6-trimethylphenyl ester, (meth)acrylamide dihydrogen phosphates, such as e.g. 6-methacrylamidohexyl- or 1,3-bis(methacrylamido)-propan-2-yl-dihydrogen phosphate, and mixtures thereof. These particularly preferred acid-group-containing monomers are characterized by a high hydrolytic stability.

The compositions according to the invention can advantageously additionally contain an initiator for the radical photopolymerization in addition to the initiator system according to the invention. Such compositions are dual-curing, i.e. they can be cured both chemically and by light. Preferred photoinitiators are benzophenone, benzoin as well as their derivatives, $\alpha$-diketones and their derivatives, such as 9,10-phenanthrenequinone, 1-phenyl-propane-1,2-dione, diacetyl and 4,4'-dichlorobenzil. Camphorquinone (CQ) and 2,2-dimethoxy-2-phenyl-acetophenone in combination with amines as reducing agent, such as e.g. 4-(dimethylamino)-benzoic acid ethyl ester (EDMAB), or N,N-dimethylaminoethyl, methacrylate are preferably used.

Compositions which do not contain amines are preferred according to the invention. Norrish type I photoinitiators are therefore particularly preferred. Norrish type I photoinitiators do not require an amine component.

Preferred Norrish type I photoinitiators are acyl- or bisacylphosphine oxides. Monoacyltrialkylgermane, diacyldialkylgermane and tetraacylgermane compounds, such as e.g. benzoyltrimethylgermane, dibenzoyldiethylgermane, bis(4-methoxybenzoyl)diethylgermane (Ivocerin®), tetrabenzoylgermane and tetrakis(o-methylbenzoyl)germane are particularly preferred.

Moreover, mixtures of the different photoinitiators can also be used, such as e.g. bis(4-methoxybenzoyl)diethylgermane or tetrakis(o-methylbenzoyl)germane in combination with camphorquinone and 4-dimethylaminobenzoic acid ethyl ester.

The compositions according to the invention can moreover advantageously contain one or more organic or inorganic fillers. Particulate fillers are preferred. Filler-containing compositions are particularly suitable as dental fixing cements or filling composites.

Preferred inorganic fillers are oxides, such as $SiO_2$, $ZrO_2$ and $TiO_2$ or mixed oxides of $SiO_2$, $ZrO_2$, $ZnO$ and/or $TiO_2$, nanoparticulate or microfine fillers, such as pyrogenic silica or precipitated silica, glass powders, such as quartz, glass ceramic, borosilicate or radiopaque glass powders, preferably barium or strontium aluminium silicate glasses, and radiopaque fillers, such as ytterbium trifluoride, tantalum(V) oxide, barium sulfate or mixed oxides of $SiO_2$ with ytterbium(III) oxide or tantalum(V) oxide. The dental materials according to the invention can furthermore contain fibrous fillers, nanofibres, whiskers or mixtures thereof.

Preferably the oxides have a particle size of from 0.010 to 15 μm, the nanoparticulate or microfine fillers have a particle size of from 10 to 300 nm, the glass powders have a particle size of from 0.01 to 15 μm, preferably of from 0.2 to 1.5 μm, and the radiopaque fillers have a particle size of from 0.2 to 5 μm.

Particularly preferred fillers are mixed oxides of $SiO_2$ and $ZrO_2$, with a particle size of from 10 to 300 nm, glass powders with a particle size of from 0.2 to 1.5 μm, in particular radiopaque glass powders of e.g. barium or strontium aluminium silicate glasses, and radiopaque fillers with a particle size of from 0.2 to 5 μm, in particular ytterbium trifluoride and/or mixed oxides of $SiO_2$ with ytterbium(III) oxide.

Moreover, ground prepolymers or pearl polymers (isofillers) are suitable as filler. These can consist exclusively of organic polymers, or organic polymers which themselves are filled with inorganic fillers such as radiopaque glass powder(s) and ytterbium trifluoride. The above-defined monomers and fillers are suitable for the preparation of the ground prepolymers and pearl polymers. Compositions for the production of full dentures preferably contain as fillers exclusively organic fillers, particularly preferably ground polymers or pearl polymers based on polymethyl methacrylate (PMMA), quite particularly preferably pearl polymers based on PMMA.

Unless otherwise stated, all particle sizes are weight-average particle sizes, wherein the particle-size determination in the range of from 0.1 μm to 1000 μm is effected by means of static light scattering, preferably using an LA-960 static laser scattering particle size analyzer (Horiba, Japan). Here, a laser diode with a wavelength of 655 nm and an LED with a wavelength of 405 nm are used as light sources. The use of two light sources with different wavelengths makes it possible to measure the entire particle-size distribution of a sample in only one measurement pass, wherein the measurement is carried out as a wet measurement. For this, a 0.1 to 0.5% aqueous dispersion of the filler is prepared and the scattered light thereof is measured in a flow cell. The scattered-light analysis for calculating particle size and particle-size distribution is effected in accordance with the Mie theory according to DIN/ISO 13320.

Particle sizes smaller than 0.1 μm are preferably determined by means of dynamic light scattering (DLS). The measurement of the particle size in the range of from 5 nm to 0.1 μm is preferably effected by dynamic light scattering (DLS) of aqueous particle dispersions, preferably with a Malvern Zetasizer Nano ZS (Malvern Instruments, Malvern UK) with an He—Ne laser with a wavelength of 633 nm, at a scattering angle of 90° at 25° C.

Particle sizes smaller than 0.1 μm can also be determined by means of SEM or TEM spectroscopy. The transmission electron microscopy (TEM) is preferably carried out with a Philips CM30 TEM at an accelerating voltage of 300 kV. For the preparation of the samples, drops of the particle dispersion are applied to a 50 Å thick copper grid (mesh size 300), which is coated with carbon, and then the solvent is evaporated.

The light scattering decreases as the particle size decreases, but fillers with a small particle size have a greater thickening action. The fillers are divided according to their particle size into macrofillers and microfillers, wherein fillers with an average particle size of from 0.2 to 10 μm are called macrofillers and fillers with an average particle size of from approx. 5 to 100 nm are called microfillers. Macrofillers are obtained e.g. by grinding e.g. quartz, radiopaque glasses, borosilicates or ceramic and usually consist of splintery parts. Microfillers such as mixed oxides can be prepared e.g. by hydrolytic co-condensation of metal alkoxides.

To improve the bond between the filler particles and the crosslinked polymerization matrix, the fillers are preferably surface-modified, particularly preferably by silanization, quite particularly preferably by radically polymerizable silanes, in particular with 3-methacryloyloxypropyltrimethoxysilane. For the surface-modification of non-silicate fillers, e.g. of $ZrO_2$ or $TiO_2$, functionalized acidic phosphates, such as e.g. 10-methacryloyloxydecyl dihydrogen phosphate can also be used.

Moreover, the compositions according to the invention can contain one or more further additives, preferably stabilizers, colorants, microbiocidal active ingredients, fluoride-ion-releasing additives, foaming agents, optical brighteners, plasticizers and/or UV absorbers.

Compositions which Contain
(a) 0.01 to 5 wt.-%, preferably 0.05 to 4.0 wt.-% and particularly preferably 0.1 to 3.0 wt.-% hydroperoxide, preferably CHP,
(b) 0.001 to 3.0 wt.-%, preferably 0.005 to 2.0 wt.-% and particularly preferably 0.005 to 0.50 wt.-% peroxide, preferably DBPO,
(c) 0.001 to 5.0 wt.-%, preferably 0.003 to 4.0 wt.-%, particularly preferably 0.005 to 3.0 wt.-% thiourea and/or thiourea derivative,
(d) 0.0001 to 1 wt.-%, preferably 0.0005 to 0.5 wt.-%, particularly preferably 0.0007 to 0.02 wt.-% transition metal compound,
(e) 5 to 95 wt.-%, preferably 10 to 95 wt.-% and particularly preferably 10 to 90 wt.-% radically polymerizable monomer,
(f) 0 to 85 wt.-% filler, and
(g) 0.01 to 5 wt.-%, preferably 0.1 to 3 wt.-% and particularly preferably 0.1 to 2 wt.-% additive
are preferred according to the invention.

All quantities herein are relative to the total mass of the composition, unless otherwise stated.

The filling level is geared towards the desired intended use of the material. Preferably filling composites have a filler content of from 50 to 85 wt.-%, particularly preferably 70 to 80 wt.-%, and dental cements have a filler content of from 10 to 70 wt.-%, particularly preferably 60 to 70 wt.-%.

Those compositions which consist of the named substances are particularly preferred. Furthermore, those compositions in which the individual components are in each case selected from the above-named preferred and particularly preferred substances are preferred. In all cases, an individual component or a mixture of several components, thus for example a mixture of monomers, can in each case be used.

The compositions according to the invention are particularly suitable as dental materials, in particular as dental cements, filling composites and veneering materials as well as materials for the production of prostheses, artificial teeth, inlays, onlays, crowns and bridges. The compositions are suitable primarily for intraoral application by the dentist for the restoration of damaged teeth, i.e. for therapeutic application, e.g. as dental cements, filling composites and veneering materials. However, they can also be used non-therapeutically (extraorally), for example in the production or repair of dental restorations, such as prostheses, artificial teeth, inlays, onlays, crowns and bridges.

The compositions according to the invention are moreover suitable for the production of shaped bodies for dental, but also for non-dental purposes, which can be produced e.g. by means of casting, compression moulding and in particular by additive processes such as 3D printing.

The invention is explained in more detail in the following with reference to embodiment examples:

EXAMPLES

Example 1

Chemically Curing Cements Based on CHP, ATU and DBPO

Resin mixtures were prepared by mixing the dimethacrylates UDMA (addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), D3MA (1,10-decanediol dimethacrylate), GDMA (glycerol-1,3-dimethacrylate) and the monofunctional monomers CMP-1E (p-cumylphenoxyethylene glycol methacrylate) and MDP (10-methacryloyloxydecyl dihydrogen phosphate) as well as the stabilizer BHT (2,6-di-tert.-butyl-4-methylphenol), the initiator components CHP (cumene hydroperoxide, 80%), DBPO (dibenzoyl peroxide, 50%), copper(I) acetylacetonate (Cuacac) and ATU (acetyl thiourea).

These were mixed with the fillers $YbF_3$ (ytterbium fluoride) and Spherosil SiO2-ZrO2 sil. (silanized $SiO_2$—$ZrO_2$ mixed oxide, Transparent Materials) in order to obtain the filler-containing catalyst pastes Cat-1 and Cat-2 as well as the filler-containing base pastes Base-1 and Base-2 specified in Table 1.

TABLE 1

Composition of the catalyst paste Cat-1 as well as of the base pastes Base-1 and Base-2 (figures in wt.-%)

| Component | Cat-1 | Cat-2 | Base-1 | Base-2 |
|---|---|---|---|---|
| UDMA | 7.93 | 7.93 | 9.23 | 9.23 |
| V-380 | 6.34 | 6.34 | 7.38 | 7.38 |
| GDMA | 6.34 | 6.34 | 7.38 | 7.38 |
| D3MA | 4.76 | 4.776 | 5.53 | 5.53 |
| CMP-1E | 6.35 | 6.35 | 7.38 | 7.38 |
| MDP | 4.13 | 4.13 | — | — |
| BHT | 0.038 | 0.038 | 0.038 | 0.04 |
| CHP (80%) | 1.596 | 1.596 | — | — |
| DBPO (50%) | 0.016 | — | — | — |
| Cuacac | — | — | — | 7 ppm |
| ATU | — | — | 0.56 | 0.56 |
| $YbF_3$[1] | 20 | 20 | 20 | 20 |
| Spherosil[2] | 42.50 | 42.50 | 42.50 | 42.50 |

[1] average particle size: 250 nm
[2] silanized $SiO_2$—$ZrO_2$ mixed oxide (Transparent Materials), primary particle size $d_{50}$ = 60-80 nm, average particle size ≤ 6 μm The catalyst paste Cat-1 was blended in each case in a 1:1 volume ratio with the base pastes Base-1 and Base-2. To determine the mechanical properties of the cements C-1 and C-2 obtained here, test pieces were produced and their flexural strength and flexural modulus of elasticity were determined according to the EN ISO-4049 standard (Dentistry—Polymer-based filling, restorative and luting materials). The results are specified in Table 2.

The catalyst paste Cat-2 was blended with the base paste Base-1 in a 1:1 volume ratio.

Then test pieces were produced from the obtained cement C-3 and the flexural strength and the flexural modulus of elasticity were determined in the manner described above. The results are likewise specified in Table 2.

A comparison of the results for C-1 and C-3 shows that the addition of the peroxide DBPO leads to a clear improvement in the mechanical properties of the composite cement. A comparison of the results for C-1 and C-2 shows that the mechanical properties were able to be quite substantially improved again by the addition of the transition metal compound Cuacac.

TABLE 2

Flexural strength (FS, MPa) and flexural modulus of elasticity (FM, GPa) of the cements C-1, C-2 and C-3

| | C-1*) (Cat-1 + Base-1) | C-2 (Cat-1 + Base-2) | C-3*) (Cat-2 + Base-1) |
|---|---|---|---|
| FS | 60 | 101 | 63 |
| Modulus of elasticity | 2.94 | 5.69 | 1.84 |

*)Comparison example

Finally, a catalyst paste Cat-3 was prepared which contained 0.2% DBPO but no CHP. Cat-3 did not harden, either after mixing with Base-1 or after mixing with Base-2.

The invention claimed is:

1. Radically polymerizable dental material, which comprises a combination of a thiourea derivative and a hydroperoxide as initiator system for the radical polymerization, characterized in that it additionally comprises at least one peroxide in a quantity of from 1 to 15 wt.-% relative to the mass of the hydroperoxide and at least one transition metal compound but does not comprise amines.

2. Dental material according to claim 1, which comprises a compound of the formula R—$(OOH)_n$, in which R is an aliphatic or aromatic hydrocarbon radical and n is 1 or 2, as hydroperoxide.

3. Dental material according to claim 2, which comprises t-amyl hydroperoxide, 1,1,3,3-tetramethylbutyl hydroperoxide, t-butyl hydroperoxide, t-hexyl peroxide, 2,5-dimethyl-2,5-di(hydroperoxy)hexane, diisopropylbenzene monohydroperoxide, paramenthane hydroperoxide, p-isopropylcumene hydroperoxide, cumene hydroperoxide (CHP), or a mixture thereof, as hydroperoxide.

4. Dental material according to claim 1, which comprises α,α-bis(t-butylperoxy)-diisopropylbenzene, dicumene peroxide, 2,5-dimethyl-2,5-bis(t-butylperoxy)hexane, t-butyl cumyl peroxide, di-t-butyl peroxide, 2,5-dimethyl-2,5-bis(t-butylperoxy)hexyne-3 or a mixture thereof, as peroxide.

5. Dental material according to claim 1, which comprises a diacyl peroxide comprising isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide, benzoyl peroxide (DBPO), or a mixture thereof, as peroxide.

6. Dental material according to claim 1, which comprises allyl thiourea, pyridyl thiourea, phenyl thiourea, hexanoyl thiourea, acetyl thiourea (ATU), or a mixture thereof, as thiourea derivative.

7. Dental material according to claim 1, which comprises a compound of a transition metal which has at least two stable oxidation states comprising a compound of copper, iron, cobalt, nickel, manganese or a mixture thereof, as transition metal compound.

8. Dental material according to claim 1, which comprises
0.01 to 5.0 wt.-% hydroperoxide, relative to the total mass of the material,
25 to 100 mol-% thiourea derivative, relative to the molar quantity of hydroperoxide,
1 to 15 wt.-% peroxide, relative to the mass of the hydroperoxide.

9. Dental material according to claim 1, which comprises
0.05 to 4.0 wt.-% hydroperoxide, relative to the total mass of the material,
50 to 100 mol-% thiourea derivative, relative to the molar quantity of hydroperoxide,
1 to 10 wt.-% peroxide, relative to the mass of the hydroperoxide.

10. Dental material according to claim 1, which comprises
0.1 to 3.0 wt.-% hydroperoxide, relative to the total mass of the material,
an equimolar quantity of thiourea derivative, relative to the molar quantity of hydroperoxide,
2 to 8 wt.-% peroxide, relative to the mass of the hydroperoxide.

11. Dental material according to claim 1, which additionally comprises at least one radically polymerizable monomer comprising at least one mono- or multifunctional (meth)acrylate, at least one dimethacrylate or a mixture of mono- and dimethacrylates.

12. Dental material according to claim 11, which comprises methyl, ethyl, 2-hydroxyethyl, butyl, benzyl, tetrahydrofurfuryl or isobornyl (meth)acrylate, p-cumylphenoxyethylene glycol methacrylate (CMP-1E), 2-(2-biphenyloxy)ethyl methacrylate, bisphenol A dimethacrylate, bis-GMA (an addition product of methacrylic acid and bisphenol A diglycidyl ether), ethoxylated or propoxylated bisphenol A dimethacrylate, 2-[4-(2-methacryloyl-oxyethoxyethoxy)phenyl]-2-[4-(2-methacryloyloxyethoxy)phenyl]propane, 2,2-bis-[4-(2-methacryloxypropoxy)phenyl]propane, UDMA (an addition product of 2-hydroxyethyl methacrylate and 2,2,4-trimethylhexamethylene-1,6-diisocyanate), V-380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), di-, tri- or tetraethylene glycol dimethacrylate, trimethylolpropane trimethacrylate, pentaerythritol tetramethacrylate, glycerol di- and trimethacrylate, 1,4-butanediol dimethacrylate, 1,10-decanediol dimethacrylate (D3MA), bis(methacryloyloxymethyl)tricyclo-[5.2.1.02,6]decane (DCP), a polyethylene glycol or polypropylene glycol dimethacrylate, polyethylene glycol 200 dimethacrylate, polyethylene glycol 400 dimethacrylate (PEG 200 DMA or PEG 400 DMA), 1,12-dodecanediol dimethacrylate or a mixture thereof as radically polymerizable monomer.

13. Dental material according to claim 11, which additionally comprises at least one acid-group-containing radically polymerizable monomer, a polymerizable carboxylic acid, phosphonic acid, a polymerizable phosphoric acid ester or an anhydride of these substances.

14. Dental material according to claim 1, which additionally comprises at least one organic or inorganic filler comprising one or more of an oxide, $SiO_2$, $ZrO_2$ or $TiO_2$ or a mixed oxide of $SiO_2$, $ZrO_2$, ZnO and/or $TiO_2$, a nanoparticulate or microfine filler, pyrogenic silica or precipitated silica, glass powders, quartz, glass ceramic or radiopaque glass powder, barium or strontium aluminium silicate glass powder, a radiopaque filler, ytterbium trifluoride, tantalum (V) oxide, barium sulfate, a mixed oxide of $SiO_2$ with ytterbium(III) oxide or tantalum(V) oxide, a ground prepolymer or a pearl polymer.

15. Dental material according to claim 1, comprising
(a) 0.01 to 5 wt.-% hydroperoxide,
(b) 0.001 to 3.0 wt.-% peroxide,
(c) 0.001 to 5.0 wt.-% thiourea derivative,
(d) 0.0001 to 1 wt.-% transition metal compound,
(e) 5 to 95 wt.-% radically polymerizable monomer,
(f) 0 to 85 wt.-% filler, and
(g) 0.01 to 5 wt.-% additive,
in each case relative to the total mass of the material.

16. Dental material according to claim 1, comprising
(a) 0.05 to 4.0 wt.-% hydroperoxide,
(b) 0.005 to 2.0 wt.-% peroxide, (c) 0.003 to 4.0 wt.-% thiourea derivative,
(d) 0.0005 to 0.5 wt.-% transition metal compound,
(e) 10 to 95 wt.-% radically polymerizable monomer,
(f) 0 to 85 wt.-% filler, and
(g) 0.1 to 3 wt.-% additive,
in each case relative to the total mass of the material.

17. Dental material according to claim 1, comprising
(a) 0.1 to 3.0 wt.-% hydroperoxide comprising CHP,
(b) 0.005 to 0.50 wt.-% peroxide comprising DBPO,
(c) 0.005 to 3.0 wt.-% thiourea derivative,
(d) 0.0007 to 0.02 wt.-% transition metal compound,
(e) 10 to 90 wt.-% radically polymerizable monomer,
(f) 0 to 85 wt.-% filler, and
(g) 0.1 to 2 wt.-% additive,
in each case relative to the total mass of the material.

18. Dental material according to claim 15, which comprises 50 to 85 wt.-% filler.

19. Dental material according to claim 1 for therapeutic application as dental cement, filling composite or veneering material.

20. Dental material according to claim 1 for non-therapeutic application in the production or repair of dental restorations comprising prostheses, artificial teeth, inlays, onlays, crowns, bridges and full dentures.

21. Dental material according to claim 15, which comprises 10 to 70 wt.-% filler.

* * * * *